United States Patent
Choi et al.

(10) Patent No.: US 8,129,064 B2
(45) Date of Patent: Mar. 6, 2012

(54) METHOD AND APPARATUS FOR MEASURING METHANOL VAPOR CONCENTRATION, METHOD OF CONTROLLING METHANOL VAPOR CONCENTRATION IN A FUEL CELL, AND FUEL CELL USING THE SAME

(75) Inventors: Kyoung-hwan Choi, Suwon-si (KR); Sang-Kyun Kang, Seoul (KR); Jin-ho Kim, Seoul (KR); Soon-ho Song, Seoul (KR); Jin-hwa Chung, Seoul (KR)

(73) Assignees: Samsung SDI Co., Ltd., Suwon-si, Gyeonggi-do (KR); Industry-Academic Cooperation Foundation, Younsei University, Seoul (KR)

( * ) Notice: Subject to any disclaimer, the term of this patent is extended or adjusted under 35 U.S.C. 154(b) by 316 days.

(21) Appl. No.: 12/468,388

(22) Filed: May 19, 2009

(65) Prior Publication Data
US 2010/0015478 A1   Jan. 21, 2010

(30) Foreign Application Priority Data
Jul. 18, 2008   (KR) ................. 10-2008-0070169

(51) Int. Cl.
*H01M 8/04* (2006.01)
*G01J 5/02* (2006.01)
(52) U.S. Cl. ............... 429/444; 429/448; 250/341.1; 250/343
(58) Field of Classification Search .......... 429/443, 429/444, 448; 250/341.1, 343
See application file for complete search history.

(56) References Cited

U.S. PATENT DOCUMENTS

| | | | | |
|---|---|---|---|---|
| 5,239,860 A | * | 8/1993 | Harris et al. | 73/61.48 |
| 5,351,198 A | * | 9/1994 | Adachi et al. | 702/24 |
| 6,701,256 B2 | * | 3/2004 | Stedman et al. | 702/24 |
| 2006/0019135 A1 | * | 1/2006 | Curello et al. | 429/22 |
| 2008/0118783 A1 | * | 5/2008 | Cetegen et al. | 429/12 |

OTHER PUBLICATIONS

P. M. Chu, F. R. Guenther, G. C. Rhoderick, and W. J. Lafferty. The NIST Quantitative Infrared Database, J. Res. Natl. Inst. Stand. Technol. 1999, 104, 1, 59-81.*
Skoog, Holler, and Crouch. Principles of Instrumental Analysis, 6$^{th}$ Ed. 2007, Chapters 3 and partial Chapter 4, p. 336-373.*
J. Chung, S. Heo, S. Song, J. Kim, S. Kang, and K. H. Choi. Measuring Methanol Concentrations in a Vapor-Fed Direct Methanol Fuel Cell Using Laser Absorption Spectroscopy, J. Electrochem. Soc. 2010, 157, 3, B320-B326.*

* cited by examiner

*Primary Examiner* — Jerry Lorengo
*Assistant Examiner* — Carlos Barcena
(74) *Attorney, Agent, or Firm* — Lee & Morse, P.C.

(57) ABSTRACT

A method of measuring methanol vapor concentration on a real-time basis and a methanol vapor concentration measuring apparatus used in fuel cells. The method of measuring methanol vapor concentration involves using an absorption spectrometry technique, that is, after measuring intensities $I_0$ and $I_1$ of light of a laser before and after passing through a space filled with methanol vapor and into which light is irradiated, the methanol vapor concentration is calculated by substituting the intensities $I_0$ and $I_1$ into an equation defined as $I_1/I_0 = \exp(K \cdot L \cdot C)$, where K represents the absorption coefficient, L represents the length of the space through which the laser passes, and C represents the methanol vapor concentration.

6 Claims, 6 Drawing Sheets

METHOD AND APPARATUS FOR MEASURING METHANOL VAPOR CONCENTRATION, METHOD OF CONTROLLING METHANOL VAPOR CONCENTRATION IN A FUEL CELL, AND FUEL CELL USING THE SAME

CROSS-REFERENCE TO RELATED APPLICATION

This application claims the benefit of Korean Patent Application No. 2008-70169, filed Jul. 18, 2008 in the Korean Intellectual Property Office, the disclosure of which is incorporated herein by reference.

BACKGROUND OF THE INVENTION

1. Field of the Invention

Aspects of the present inventive concept relate to a method of measuring methanol vapor concentration on a real-time basis, and to a fuel cell in which a method of controlling the methanol vapor concentration employs the method of measuring methanol vapor concentration.

2. Description of the Related Art

Methanol is widely used in various industrial fields for various purposes. For example, methanol is used as a raw material for manufacturing compounds such as synthetic dyes, medical supplies, or perfumes, as well as a fuel for generating electricity from a fuel cell such as a direct methanol fuel cell (DMFC).

Meanwhile, recently, a method of measuring methanol vapor concentration on a real-time basis has become necessary. In a working environment where methanol is used as a raw material, since methanol is colorless and its inhalation in large amounts is harmful to humans, a rapid emergency measure can be taken if the methanol vapor concentration mixed in the air can be measured on a real-time basis and is too high. Also, in the case of a fuel cell, such as a DMFC, research is being conducted on fuel cells in which methanol vapor is supplied, instead of liquid methanol. In a methanol vapor fuel cell, if an excessive amount of methanol is supplied to the fuel cell, methanol vapor that should have reacted in the anode can create a cross-over situation, where methanol flows into the cathode and combusts directly, thereby reducing the performance of the fuel cell. Conversely, if an insufficient amount of methanol vapor is supplied to the fuel cell, the fuel cell cannot perform properly. Therefore, appropriate concentration control is necessary. However, so far, a method of measuring the methanol vapor concentration on a real-time basis has not been developed. If a method of measuring methanol vapor concentration on a real-time basis is developed, the method can be utilized in various industrial fields that use methanol.

SUMMARY OF THE INVENTION

To address the above and/or other problems, a method of measuring methanol vapor concentration on a real-time basis, and a fuel cell in which a method of controlling the methanol vapor concentration employs the method of measuring methanol vapor concentration are disclosed.

A method of measuring methanol vapor concentration includes: irradiating light from a laser into a space filled with methanol vapor; measuring intensities $I_0$ and $I_1$ of light of the laser respectively before ($I_0$) and after ($I_1$) passing through the space; and calculating the methanol vapor concentration by substituting the intensities $I_0$ and $I_1$ into an equation defined as $I_1/I_0 = \exp(K \cdot L \cdot C)$ where K represents the absorption coefficient of methanol vapor, L represents the length of the space through which the laser passes, and C represents the methanol vapor concentration to be measured.

The absorption coefficient K may be 0.005335 torr$^{-1}$ cm$^{-1}$, and may have a wavelength of 3.39 μm. The absorption coefficient K may be obtained by substituting the intensities $I_0$ and $I_1$ of light into the equation, as measured by irradiating a laser into a space which is filled with methanol vapor, once the methanol vapor concentration is known.

A method of controlling methanol vapor concentration of a fuel cell includes: preparing a fuel cell stack having an anode, an electrolyte membrane, and a cathode; supplying methanol vapor to the anode by injecting methanol into the fuel cell stack; irradiating laser light into the space of the fuel cell stack where the methanol vapor is supplied; measuring intensities $I_0$ and $I_1$ of the laser light respectively before and after passing through the space; calculating the methanol vapor concentration by substituting the intensities $I_0$ and $I_1$ into an equation defined as $I_1/I_0 = \exp(K \cdot L \cdot C)$ where K represents the absorption coefficient of methanol vapor, L represents the length of the space through which the laser passes, and C represents the methanol vapor concentration to be measured; and controlling the amount of fuel supplied into the fuel cell stack as a function of the calculated methanol vapor concentration.

The absorption coefficient K may be 0.005335 torr$^{-1}$ cm$^{-1}$, and may have a wavelength of 3.39 μm. The absorption coefficient K may be obtained by substituting the intensities $I_0$ and $I_1$ of light measured by irradiating laser into the space which is filled with methanol vapor, the concentration of which is known. The method may further include measuring the concentration of methanol vapor, which is formed due to cross-over, in a space above the cathode which is located opposite to the space above the anode where methanol enters the fuel cell.

An apparatus for measuring methanol vapor concentration includes: a cell having a space for methanol vapor; a laser unit that irradiates light into the space; measuring units that respectively measure intensities $I_0$ and $I_1$ of the irradiated light before and after passing through the space; a computing unit that calculates the methanol vapor concentration by substituting the intensities $I_0$ and $I_1$ into an equation defined as $I_1/I_0 = \exp(K \cdot L \cdot C)$ where K represents an absorption coefficient of methanol vapor and is 0.005335 torr$^{-1}$ cm$^{-1}$, L represents a length of the space through which the laser passes, and C represents the methanol vapor concentration to be measured.

The absorption coefficient K may be 0.005335 torr$^{-1}$ cm$^{-1}$, and may have a wavelength of 3.39 μm. The absorption coefficient K may be obtained by substituting the intensities $I_0$ and $I_1$ of light measured by irradiating laser into the space which is filled with methanol vapor, the concentration of which is known.

A fuel cell may include: a fuel cell stack having an anode, an electrolyte membrane, and a cathode; a fuel injection unit that injects methanol into the fuel cell stack in order for the methanol to be supplied to the anode; a methanol vapor concentration measuring apparatus that measures methanol vapor concentration by irradiating a laser into the space where methanol vapor injected to the fuel cell stack is supplied to the anode; and a controller that controls the amount of methanol supplied to the fuel cell stack as a function of the measured methanol vapor concentration.

The methanol vapor concentration measuring apparatus may comprise: a laser unit that irradiates light into the space of the fuel cell stack where the methanol vapor is supplied; measuring units that respectively measure intensities $I_0$ and $I_1$ of the irradiated light before and after passing through the space; and a computing unit that calculates the methanol vapor concentration by substituting the intensities $I_0$ and $I_1$ into an equation defined as $I_1/I_0 = \exp(K \cdot L \cdot C)$ where K represents the absorption coefficient of methanol vapor, L represents the length of the space through which the laser passes, and C represents the methanol vapor concentration to be measured.

The absorption coefficient K may be 0.005335 $torr^{-1}$ $cm^{-1}$, and may have a wavelength of 3.39 μm. The absorption coefficient K may be obtained by substituting the intensities $I_0$ and $I_1$ of light into the equation, measured by irradiating a laser into a space which is filled with methanol vapor, once the methanol vapor concentration is known.

The measuring units may, respectively, measure the methanol vapor concentration in the space from which methanol vapor is supplied to the anode and the methanol vapor formed due to cross-over in the space above the cathode located opposite to the anode by using the irradiated light. The methanol vapor concentration measuring apparatus may be installed in or outside the fuel cell stack.

Additional aspects and/or advantages of the invention will be set forth in part in the description which follows and, in part, will be obvious from the description, or may be learned by practice of the invention.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE EMBODIMENTS

Reference will now be made in detail to the present embodiments of the present invention, examples of which are illustrated in the accompanying drawings, wherein like reference numerals refer to the like elements throughout. The embodiments are described below in order to explain the present invention by referring to the figures.

Figure 1:
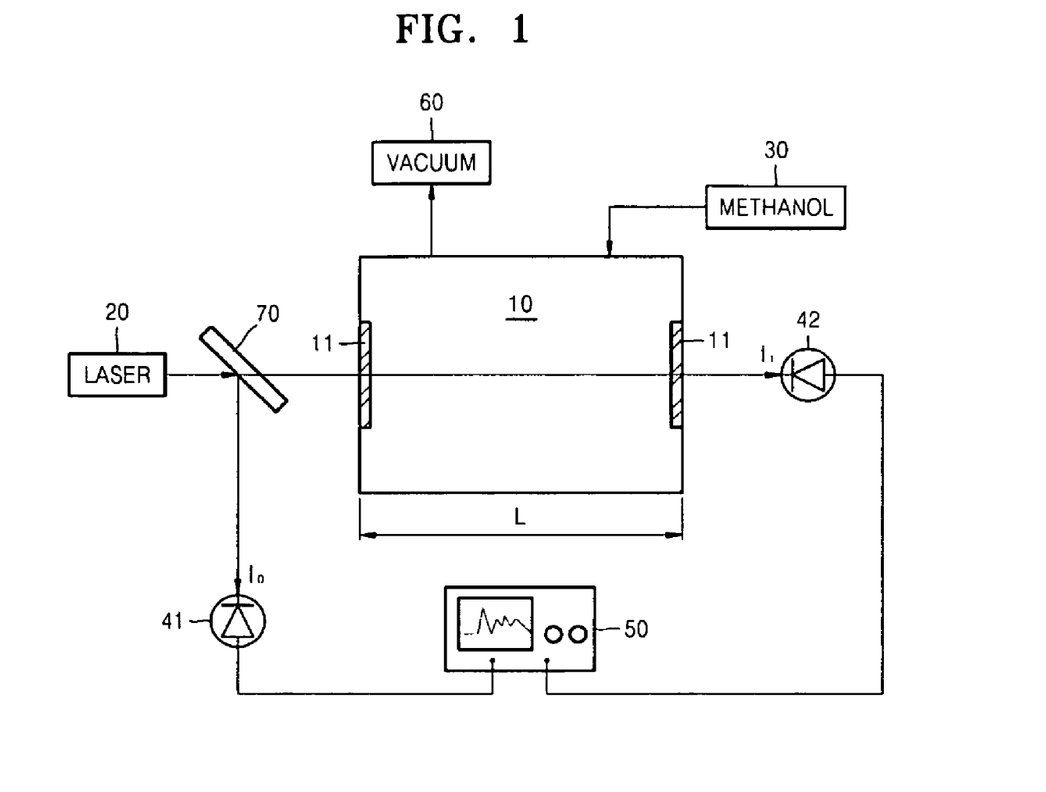
FIG. 1 is a schematic drawing of an apparatus for measuring methanol vapor concentration by using a method of measuring methanol vapor concentration, according to an embodiment of the present inventive concept.

FIG. 1 is a schematic drawing of an apparatus for measuring methanol vapor concentration by using a method of measuring methanol vapor concentration, according to an embodiment of the present inventive concept. Referring to FIG. 1, the apparatus, according to this embodiment, includes a cell 10 having a space in which methanol supplied from a methanol injection unit 30 is stored in a vapor state, a He—Ne laser 20 that generates a laser that shoots through windows 11 provided on the cell 10 and has a wavelength of 3.39 μm, first and second photodiodes 41 and 42 that respectively measure intensities $I_0$ and $I_1$ of the laser before ($I_0$) and after ($I_1$) passing through the cell 10, and a computing unit 50 to monitor measured results and yield a methanol vapor concentration from the measured results. The apparatus further includes a vacuum-maintaining unit 60 that maintains the vacuum at a constant level of 0.5 torr. In this embodiment, the vacuum-maintaining unit 60 is installed to accurately yield an absorption coefficient K of methanol vapor that is to be described later, and thus, the vacuum-maintaining unit 60 is not an essential element for measuring the methanol vapor concentration. The apparatus also includes a beam splitter 70.

The method of measuring methanol vapor concentration involves using an absorption spectrometry technique. That is, when a laser is passing through the space filled with methanol vapor, a portion of the laser is absorbed by methanol vapor molecules, and thus, there is a difference between the optical intensity difference of the laser before and after passing through the cell 10. This characteristic may be expressed as an equation $I_1/I_0 = \exp(K \cdot L \cdot C)$, where K represents the absorption coefficient of methanol vapor, L represents the length of the internal space of the cell 10 through which the laser passes, and C represents the methanol vapor concentration to be measured.

Figure 2:
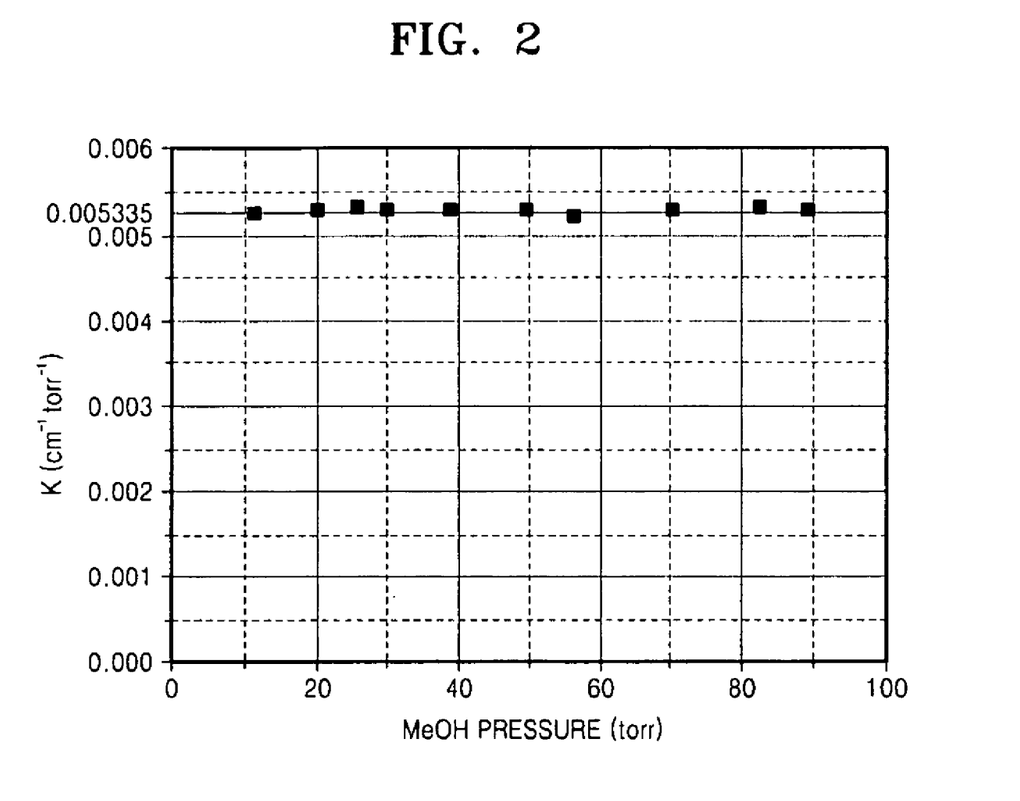
FIG. 2 is a graph showing absorption coefficients of methanol vapor concentration measured using the method of FIG. 1.

Intensities $I_0$ and $I_1$ are values measured respectively by the first and second photodiodes 41 and 42, and the length L is determined from the internal space of the cell 10. In order to obtain the methanol vapor concentration C, the absorption coefficient K must be known in advance, and then can be substituted into the above equation. However, in that case, the methanol vapor concentration C must not be an unknown. Thus, after injecting a predetermined methanol vapor concentration into the cell 10, the intensities $I_0$ and $I_1$ are measured, and afterwards, the absorption coefficient K can be calculated. FIG. 2 shows values of absorption coefficients K calculated in this way. It can be seen from FIG. 2 that almost constant absorption coefficients K are calculated although the measurements are carried out at various methanol concentrations (here, methanol vapor pressure), as long as the laser having a wavelength of 3.39 μm is used. The absorption coefficient K of 0.005335 $torr^{-1}$ $cm^{-1}$ was obtained. Thus, since it can be seen in FIG. 2 that the absorption coefficient K of the methanol vapor with respect to the laser having a wavelength of 3.39 μm is 0.005335 $torr^{-1}$ $cm^{-1}$, when the absorption coefficient K of 0.005335 $torr^{-1}$ $cm^{-1}$ is substituted into the equation above, the methanol vapor concentration C, which varies according to operating conditions, can be obtained on a real-time basis.

The method of measuring methanol vapor concentration using the above-described apparatus will now be described. First, light is irradiated onto the cell 10, where methanol is injected from the methanol injection unit 30, by operating the He—Ne laser 20. The irradiated light passes the cell 10 through the window 11, and, at this point, the intensity $I_0$ of light before passing through the cell 10 and the intensity $I_1$ of light after passing through the cell 10 are measured by the first and second photodiodes 41 and 42, respectively. The measured intensities $I_0$ and $I_1$ are transmitted to the computing unit 50 where the results are monitored on a screen and the methanol vapor concentration is simultaneously calculated by substituting the intensities $I_0$ and $I_1$ into the equation. In this way, the methanol vapor concentration can be obtained on a real-time basis, and thus, an appropriate measure can be taken.

Figure 3:
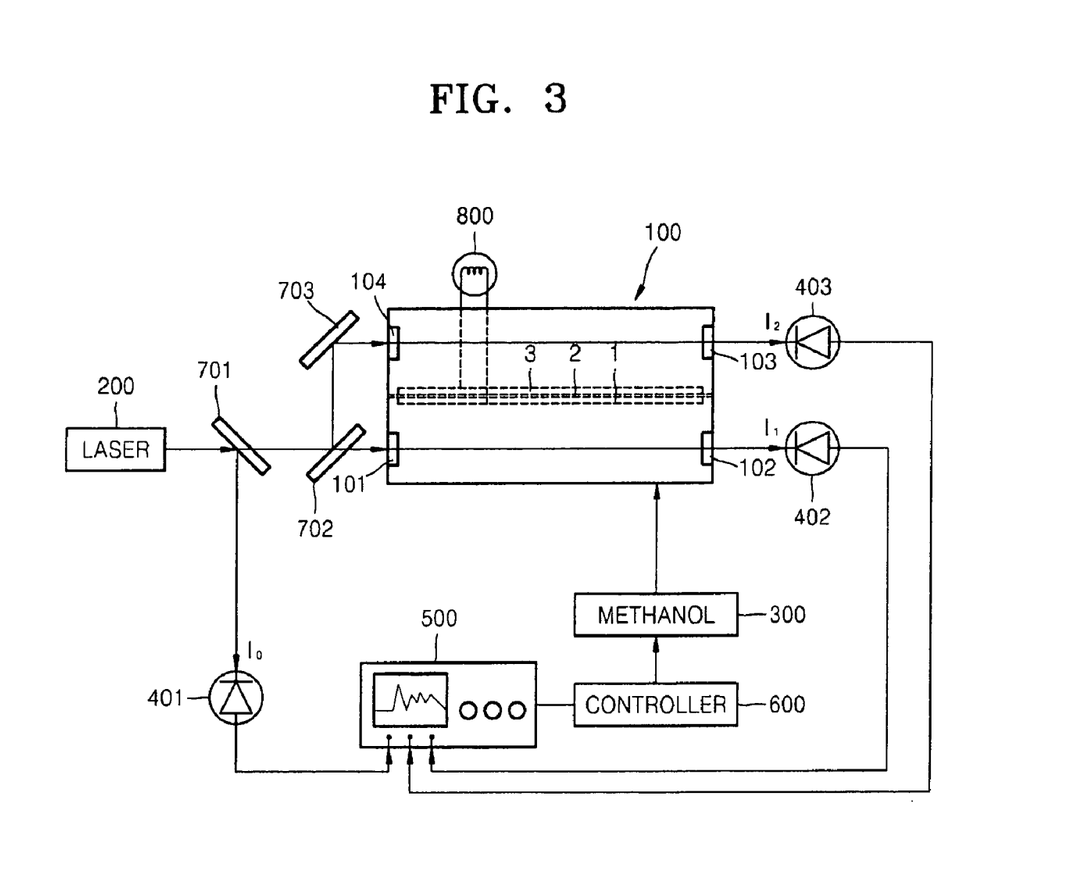
FIG. 3 is a schematic drawing of a fuel cell in which the methanol vapor concentration is controlled using the method of FIG. 1.

FIG. 3 is a schematic drawing of a fuel cell in which the methanol vapor concentration is controlled using the method of FIG. 1. The cell 10 of FIG. 1 corresponds to a fuel cell stack 100 in which an anode 1 (not shown in FIG. 1), an electrolyte membrane 2 (not shown in FIG. 1), and a cathode 3 (not shown in FIG. 1) are included. Also, the fuel cell stack 100 includes windows 101, 102, 103, and 104. Light is irradiated from a laser 200 onto the fuel cell stack 100 through the window 101 formed in the fuel cell stack 100, and the light is detected by first and second photodiodes 401 and 402. Intensities $I_0$ and $I_1$, measured by the first and second photodiodes 401 and 402, are substituted into the equation in order for a computing unit 500 to calculate the methanol vapor concentration as described above.

The values of methanol vapor concentration that are measured in this way are transmitted to a controller 600 so as to be compared to a reference range. Thus, the methanol vapor concentration is controlled in a way that, if the measured methanol vapor concentration exceeds the reference range, the amount of methanol supplied from a methanol fuel supply unit 300 is reduced, and if the measured methanol vapor concentration falls below the reference range, the amount of methanol supplied is increased. Thus, the methanol vapor concentration range can be maintained uniform by measuring the methanol vapor concentration on a real-time basis, and thus, an excessive supply or an insufficient supply of fuel can be avoided, thereby inducing stable power generation. The fuel cell further includes beam splitters 701 and 702, a mirror 703, and a load 800.

Figure 4:
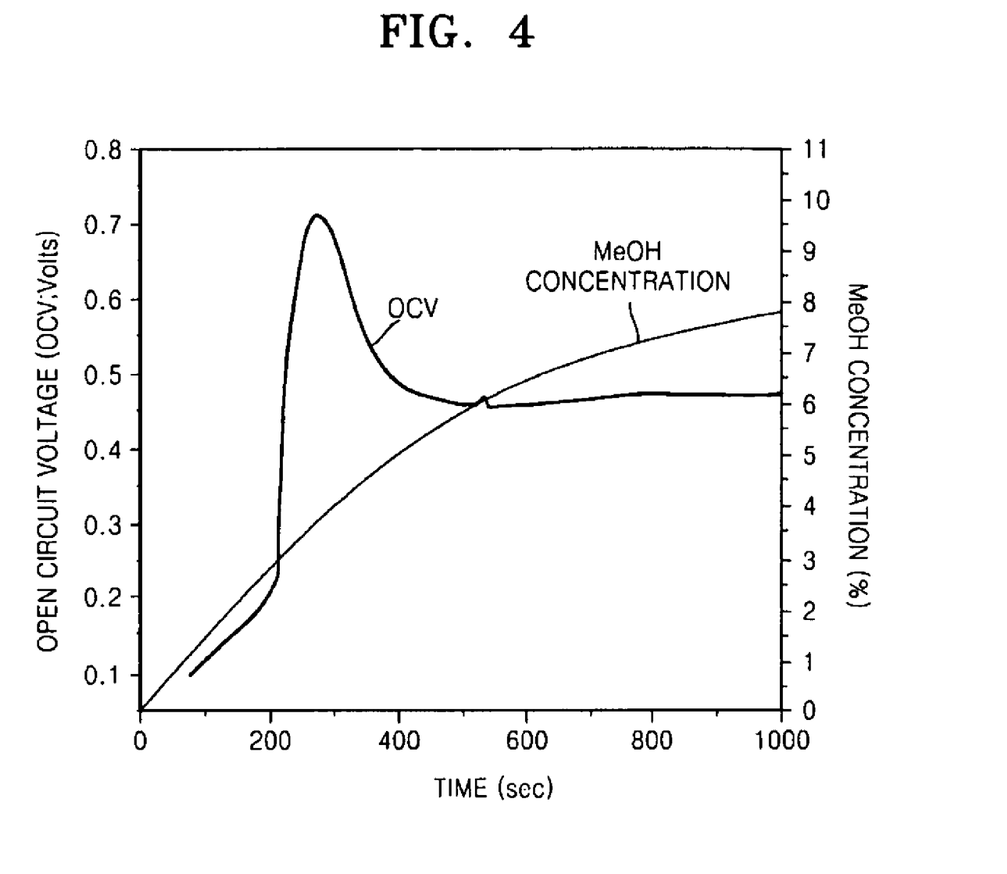
FIG. 4 is a graph showing the variation of voltage and methanol vapor concentration in the fuel cell of FIG. 3 when the fuel cell is in a no-load state.

FIG. 4 is a graph showing measurement results of output voltage and the methanol vapor concentration of the fuel cell stack 100 while supplying fuel to the anode 1 in a no-load state, that is, the load 800 is removed from the fuel cell 100 of FIG. 3. The output voltage (OCV) shows a large variation at an early stage of operation, however, after a short period of time, it can be seen that the output voltage stabilizes. The methanol vapor concentration continuously increases when the fuel supply begins. Thus, while detecting such a methanol vapor concentration variation, if the methanol vapor concentration value deviates from the reference range, as described above, the output voltage is re-stabilized accordingly by increasing or decreasing the fuel supply.

Figure 5:
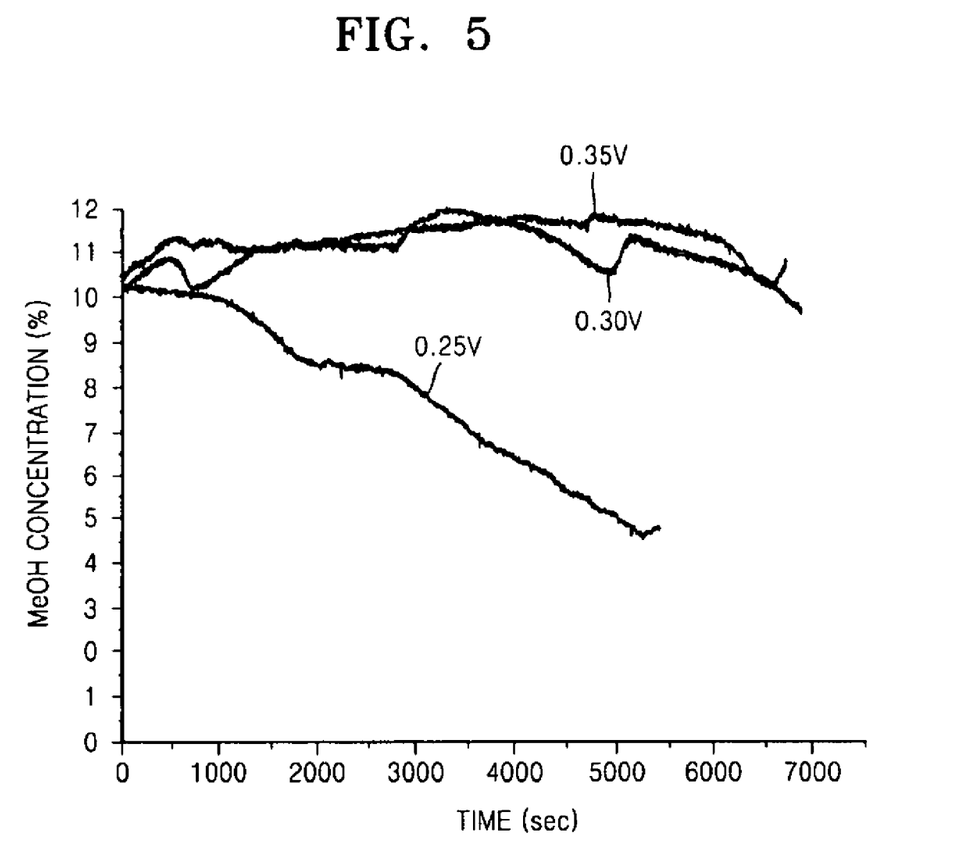
FIG. 5 is a graph showing the variation of methanol vapor concentration in the fuel cell of FIG. 3 when the fuel cell is in a load state.

FIG. 5 is a graph showing the measurement results of methanol vapor concentration in three stationary voltage states when the fuel cell of FIG. 3 is in a load state, that is, the fuel cell includes the load 800. When the constant voltages of 0.30V and 0.35V are consistently maintained, the amount of fuel injection and the amount of fuel consumption is in an equilibrium state, and thus, the methanol vapor concentration is stably maintained. However, when the constant voltage of 0.25V is consistently maintained, the methanol vapor concentration gradually reduces. This reduction is sensed as a current increase, so that fuel consumption is increased. Thus, through the methanol vapor concentration measurement on a real-time basis, a constant voltage range can be obtained in which the methanol vapor concentration can be stably maintained.

As depicted in FIG. 3, the fuel cell further includes a third photodiode 403, beside the first and second photodiodes 401 and 402, for measuring methanol vapor concentration on the cathode 3. The third photodiode 403 may be effectively used for measuring the degree of crossover, that is, the amount of methanol that combusts directly at the cathode 3 after crossing over from the anode 1. In this case also, light from the laser 200 is irradiated onto the fuel cell stack 100 through the window 104 via the mirror 703, intensities $I_0$ and $I_1$ of light before and after passing through the fuel cell stack 100 are measured respectively by the first and third photodiodes 401 and 403, and the methanol vapor concentration is calculated in the computing unit 500 using the intensities $I_0$ and $I_1$. In FIG. 3, the concentration measuring apparatus, the computing unit 500, is installed outside the fuel cell stack 100; however, the present invention is not limited thereto, and thus, the concentration measuring apparatus may be included in the fuel cell stack 100 by providing a space for installing the concentration measuring apparatus in the fuel cell stack 100. Thus, according to this embodiment, a fuel cell that can perform stably can be realized by utilizing a method of measuring methanol vapor concentration on a real-time basis and thus controlling the fuel cell.

Figure 6:
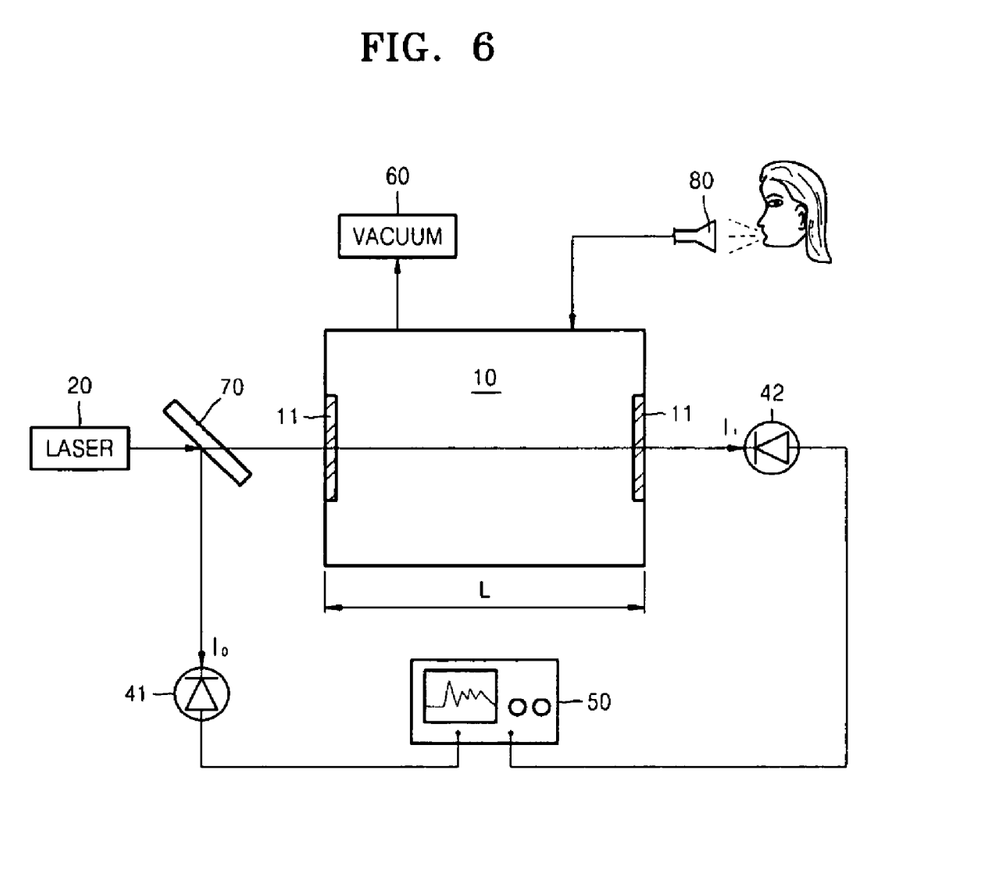
FIG. 6 is a schematic drawing showing an application of the apparatus for measuring methanol vapor concentration of FIG. 1.

Also, the apparatus for measuring methanol vapor concentration can be used as a mobile device, as shown in FIG. 6. For example, when the methanol vapor concentration in a human's breath needs to be measured, after the human breathes into a blowing tube 80 to fill the space in the cell 10 with his/her breath, the methanol vapor concentration can be measured with the same method as described above for irradiating a sample space with a laser.

Although a few embodiments of the present invention have been shown and described, it would be appreciated by those skilled in the art that changes may be made in this embodiment without departing from the principles and spirit of the invention, the scope of which is defined in the claims and their equivalents.

What is claimed is:

1. A fuel cell comprising:
   a fuel cell stack having an anode, an electrolyte membrane, and a cathode;
   a fuel injection unit that injects methanol into the fuel cell stack in order for the methanol to be supplied to the anode;
   a methanol vapor concentration measuring apparatus including a laser unit that irradiates light into the space of the fuel cell stack where the methanol vapor is supplied, measuring units that respectively measure intensities $I_0$ and $I_1$ of the irradiated light before and after passing through the space, and a computing unit that calculates the methanol vapor concentration by substitutin the intensities $I_0$ and $I_1$ into an equation defined as $I_1/I_0 = \exp(K \cdot L \cdot C)$, where K represents the absorption coefficient of methanol vapor and is 0.005335 torr$^{-1}$ cm$^{-1}$, L represents the length of the space through which the laser passes, and C represents the methanol vapor concentration to be measured, the methanol vapor concentration measuring apparatus being configured to measure methanol vapor concentration in a space by irradiating a laser into the space where methanol vapor injected into the fuel cell stack is supplied to the anode; and a controller that controls the amount of methanol into the fuel cell stack according to the measured methanol vapor concentration.

2. The fuel cell of claim 1, wherein the light of the laser has a wavelength of 3.39 μm.

3. The fuel cell of claim 1, wherein the absorption coefficient K is obtained by substituting the intensities $I_0$ and $I_1$ of light into the equation, and is measured by irradiating a laser into a space which is filled with a known methanol vapor concentration.

4. The fuel cell of claim 1, wherein the measuring units respectively measure the methanol vapor concentration in the space from which methanol vapor is supplied to the anode and measure by using the irradiated light the methanol vapor formed due to cross-over in the space above the cathode located opposite to the anode.

5. The fuel cell of claim 1, wherein the methanol vapor concentration measuring apparatus is installed in the fuel cell stack.

6. The fuel cell of claim 1, wherein the methanol vapor concentration measuring apparatus is installed outside the fuel cell stack.

* * * * *